United States Patent
Chen et al.

(10) Patent No.: US 11,673,857 B2
(45) Date of Patent: Jun. 13, 2023

(54) PREPARATION METHOD OF 1-(4-AMINO-PHENYL)CYCLOPENTANECARBONITRILE

(71) Applicant: ZHEJIANG RONGYAO BIOTECH CO., LTD., Linhai (CN)

(72) Inventors: Rener Chen, Linhai (CN); Na Zhang, Linhai (CN); Qiuhong Zhang, Linhai (CN)

(73) Assignee: ZHEJIANG RONGYAO BIOTECH CO., LTD., Linhai (CN)

( * ) Notice: Subject to any disclaimer, the term of this patent is extended or adjusted under 35 U.S.C. 154(b) by 98 days.

(21) Appl. No.: 17/448,364

(22) Filed: Sep. 22, 2021

(65) Prior Publication Data
US 2022/0177420 A1 Jun. 9, 2022

(30) Foreign Application Priority Data
Dec. 3, 2020 (CN) .......................... 202011410797.4

(51) Int. Cl.
C07C 253/30 (2006.01)
C07C 253/34 (2006.01)
B01J 21/18 (2006.01)
B01J 23/42 (2006.01)
B01J 23/44 (2006.01)

(52) U.S. Cl.
CPC ............. *C07C 253/30* (2013.01); *B01J 21/18* (2013.01); *B01J 23/42* (2013.01); *B01J 23/44* (2013.01); *C07C 253/34* (2013.01)

(58) Field of Classification Search
CPC ............................ C07C 253/30; C07C 253/34
See application file for complete search history.

(56) References Cited

FOREIGN PATENT DOCUMENTS

CN 106243031 A 12/2016

*Primary Examiner* — Sikarl A Witherspoon
(74) *Attorney, Agent, or Firm* — Bayramoglu Law Offices LLC

(57) ABSTRACT

A preparation method of 1-(4-aminophenyl)cyclopentanecarbonitrile includes the following steps: step 1: in the presence of $Li_2CuCl_4$, adding a nitrochlorobenzene-zinc reagent dropwise to a 1-chlorocyclopentanecarbonitrile solution to prepare a compound 1-(4-nitrophenyl)cyclopentanecarbonitrile; and step 2: subjecting the compound 1-(4-nitrophenyl)cyclopentanecarbonitrile obtained in step 1 to a nitroreduction reaction under the action of a catalyst to prepare the compound 1-(4-aminophenyl)cyclopentanecarbonitrile. The preparation method involves cheap and easily-available raw materials, mild reaction conditions, and convenient operations, leads to high yield, and is environmentally-friendly and suitable for industrial large-scale production.

9 Claims, No Drawings

PREPARATION METHOD OF 1-(4-AMINOPHENYL)CYCLOPEN-TANECARBONITRILE

CROSS REFERENCE TO THE RELATED APPLICATIONS

This application is based upon and claims priority to Chinese Patent Application No. 202011410797.4 filed on Dec. 3, 2020, the entire contents of which are incorporated herein by reference.

TECHNICAL FIELD

The present disclosure belongs to the technical field of pharmaceutical chemical synthesis, and relates to a preparation method of an apatinib intermediate, and in particular to a preparation method of 1-(4-aminophenyl)cyclopentanecarbonitrile.

BACKGROUND

Apatinib is the first small-molecule anti-angiogenesis targeted drug worldwide that has been proven safe and effective in the treatment of advanced gastric cancer. It is also the only oral preparation among targeted drugs for advanced gastric cancer. Clinical studies have shown that adverse reactions of apatinib are controllable, resulting in relatively high safety. Studies have also shown that apatinib also exhibits prominent therapeutic effects for breast cancer, gastric cancer, and other cancers. However, apatinib is only sold in China at present. On Mar. 1, 2017, apatinib was designated by the European Medicines Evaluation Agency (EMEA) as an orphan drug for treating gastric cancer, which accelerated the clinical research and drug development of apatinib in European Union countries.

1-(4-aminophenyl)cyclopentanecarbonitrile (ACC) is a key intermediate for apatinib synthesis, which is a white to yellow solid powder, with a molecular formula of $C_{12}H_{14}N_2$, a CAS number of 115279-73-7, and a structural formula as follows:

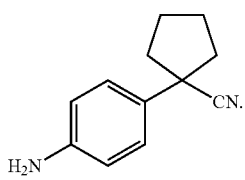

In the preparation method of 1-(4-aminophenyl)cyclopentanecarbonitrile disclosed in Chinese Patent CN106243031A on Dec. 21, 2016, phenylacetonitrile is subjected to double alkylation with 1,4-dichlorobutane or 1,4-dibromobutane to form a five-membered ring compound, and then the five-membered ring compound is subjected to nitration and reduction to obtain the apatinib intermediate 1-(4-aminophenyl)cyclopentanecarbonitrile, which involves a reaction equation as follows:

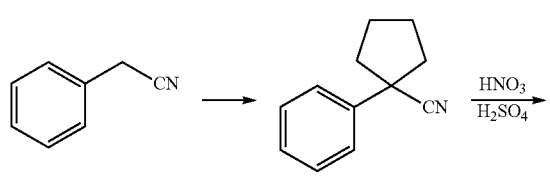

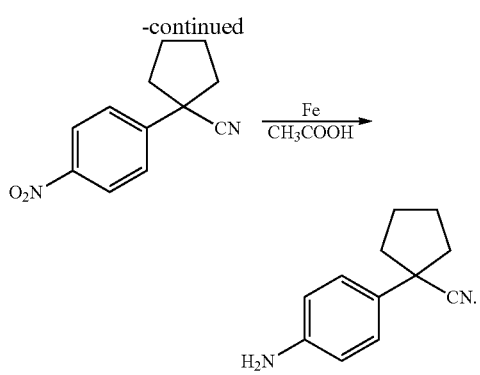

The nitration in the above route is conducted with a mixed acid solution of nitric acid and sulfuric acid, which results in the release of a large amount of heat, cannot achieve the selective production of a nitration product, and will lead to the production of some o-nitro by-products. The by-products cannot be easily removed, and need to be removed by column chromatography, which is not conducive to industrial production. Nitroreduction is conducted with iron, during which a large amount of iron sludge will be produced, causing environmental pollution, cumbersome subsequent treatment, and compromised yield.

A method of subjecting 1-phenyl-1-cyanocyclopentane to nitration and reduction to obtain 1-(4-aminophenyl)cyclopentanecarbonitrile is also disclosed in the art, which involves a reaction equation as follows:

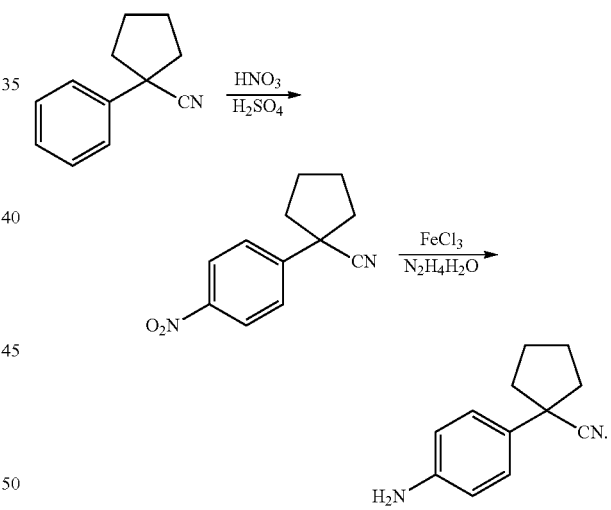

Nitration conditions in the above route are not selective and thus some o-nitro by-products will be produced. The by-products cannot be easily removed, and need to be removed by column chromatography, which is not conducive to industrial production. Nitroreduction is conducted with ferric chloride, during which a large amount of iron sludge will be produced, causing environmental pollution, cumbersome subsequent treatment, and compromised yield. A solvent used for the nitroreduction is hydrazine hydrate, which is an explosive chemical. The hydrazine hydrate, if used carelessly, may pose a great potential safety hazard.

In addition, there is a literature about subjecting p-nitrophenylacetonitrile to cyclization and reduction to obtain 1-(4-aminophenyl)cyclopentanecarbonitrile, which involves a reaction equation as follows:

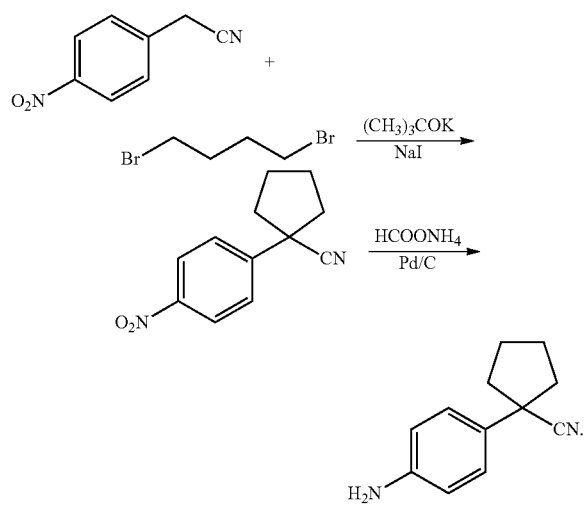

The above route does not involve nitration, but a cyclization product has low purity, and a dark green impurity is produced. The dark green impurity is difficult to remove and needs to be separated by column chromatography. Moreover, a large amount of solid wastes is produced, which is not conducive to industrial production.

Therefore, there is an urgent need to develop an environmentally-friendly preparation method of 1-(4-aminophenyl)cyclopentanecarbonitrile that involves cheap and easily-available raw materials, mild conditions, and convenient operations, leads to high yield, and is suitable for industrial large-scale production.

SUMMARY

The present disclosure is intended to overcome the technical problem in the prior art that existing preparation processes of 1-(4-aminophenyl)cyclopentanecarbonitrile involve expensive and rare raw materials, harsh reaction conditions, large potential safety hazard, easy production of by-products, and serious environmental pollution and provide an environmentally-friendly preparation method of 1-(4-aminophenyl)cyclopentanecarbonitrile that involves cheap and easily-available raw materials, mild reaction conditions, and convenient operations, leads to high yield, and is suitable for industrial large-scale production.

In order to solve the above technical problem, the present disclosure provides a preparation method of 1-(4-aminophenyl)cyclopentanecarbonitrile, including the following steps:

step 1: in the presence of $Li_2CuCl_4$, adding a solution of p-nitrochlorobenzene-zinc in a solvent B dropwise to a solution of 1-chlorocyclopentanecarbonitrile in a solvent A to prepare a compound 1-(4-nitrophenyl)cyclopentanecarbonitrile; and step 2: subjecting the compound 1-(4-nitrophenyl)cyclopentanecarbonitrile obtained in step 1 to a nitroreduction reaction in a solvent C under the action of a catalyst to prepare the compound 1-(4-aminophenyl)cyclopentanecarbonitrile;

where a reaction equation is as follows:

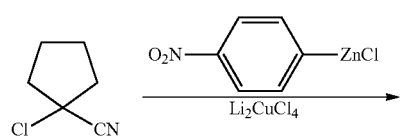

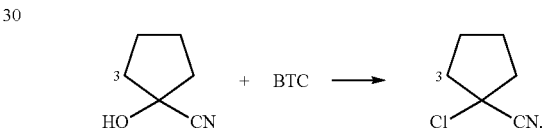

the solvent A used in step 1 is one from the group consisting of toluene, xylene, benzene, diethyl ether, chloroform, and tetrahydrofuran (THF);

the solvent B used in step 1 is one from the group consisting of toluene, diethyl ether, THF, and dimethyl sulfoxide (DMSO); and the solvent C used in step 2 is one from the group consisting of ethanol, methanol, and isobutanol.

As a further improvement of the present disclosure, in step 1, the solution of 1-chlorocyclopentanecarbonitrile in a solvent A may be prepared as follows:

adding 1-hydroxycyclopentanecarbonitrile and the solvent A into a reaction vessel, stirring, and heating to 55° C. to 60° C.; adding a solution of 10% to 17% triphosgene in the solvent A dropwise at a temperature controlled to 60° C. to 65° C.; and after the dropwise addition is completed, heating a resulting mixture to allow a reaction at reflux for 1 h to 2 h to obtain the solution of 1-chlorocyclopentanecarbonitrile in a solvent A, where a reaction equation is as follows:

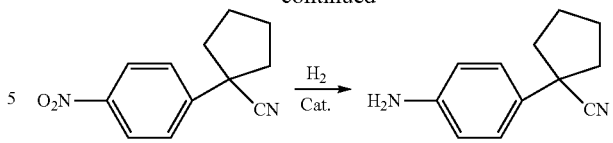

As a further improvement of the present disclosure, in step 1, the solution of p-nitrochlorobenzene-zinc in a solvent B may be prepared as follows:

adding the solvent B and a zinc powder into a reaction vessel, stirring, and heating to 45° C. to 50° C. under nitrogen protection; adding a solution of 5% to 10% p-nitrochlorobenzene in the solvent B dropwise, and stirring for 15 min to 30 min; after success initiation, further adding a solution of p-nitrochlorobenzene in the solvent B dropwise at a temperature controlled to 50° C. to 55° C.; after the dropwise addition is completed, heating a resulting mixture to allow a reaction at reflux for 1 h to 2 h; and cooling a reaction solution to 20° C. to 30° C., and subjecting the reaction solution to solid-liquid separation (SLS) to obtain the solution of p-nitrochlorobenzene-zinc in a solvent B, where a reaction equation is as follows:

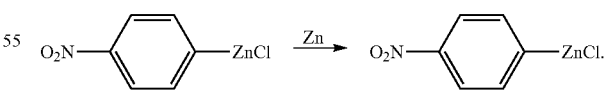

When the p-nitrochlorobenzene solution is added dropwise at a low temperature, a reaction rate is low, and a large amount of raw materials in the system will not react. When the p-nitrochlorobenzene solution is added dropwise at a temperature of 50° C. to 55° C., a residual amount of raw materials in the reaction system is less than or equal to 0.5%, and the reaction is basically complete. When the p-nitrochlorobenzene solution is added dropwise at a temperature higher than 50° C. to 55° C., a reaction rate increases, and the raw materials in the system react completely, but an impurity content in the system is high. This is because the reaction is an exothermic reaction, and due to high dropwise addition temperature and high reaction rate, heat produced during the reaction cannot be timely transferred out of the reaction system, and two nitrochlorobenzene molecules will be dechlorinated and coupled to produce by-products. According to chemical kinetics analysis, a high temperature is conducive to the intermolecular dehalogenation side reaction, and thus conducting the dropwise addition at a low temperature enabling the reaction can reduce the dehalogenation side reaction and increase the selectivity. Therefore, in this reaction, an appropriate dropwise addition temperature of the p-nitrochlorobenzene solution is 50° C. to 55° C.

As a further improvement of the present disclosure, step 1 may specifically include: adding the solution of 1-chlorocyclopentanecarbonitrile in a solvent A and the $Li_2CuCl_4$ to a reaction vessel, stirring, and cooling to 5° C. to 10° C.; adding the solution of p-nitrochlorobenzene-zinc in a solvent B dropwise at a temperature controlled to 10° C. to 15° C.; and after the dropwise addition is completed, keeping a resulting mixture at 15° C. to 20° C. for 1 h to 2 h to obtain a solution with the compound 1-(4-nitrophenyl)cyclopentanecarbonitrile.

When a reaction temperature is low, the reaction is slow and the raw materials will not completely react. When the cyclization temperature is appropriately increased, the reaction is accelerated and the reaction time is shortened. In the present disclosure, the reaction temperature is always controlled at 15° C. to 20° C., in which case, the reaction is relatively fast, and no raw materials remain in the reaction solution. If the reaction temperature is further increased, the reaction time is slightly shortened, but by-products will increase and a yield will decrease.

As a further improvement of the present disclosure, a molar ratio of the 1-hydroxycyclopentanecarbonitrile to the triphosgene may be 1:(0.35-0.55) and preferably 1:0.5.

If triphosgene is added at a too-small amount, the reaction of 1-hydroxycyclopentanecarbonitrile is incomplete, resulting in low product yield. However, when the amount of triphosgene exceeds a specified value, further increasing the amount of triphosgene will not significantly increase a yield, but lead to more impurities in a product. Therefore, the molar ratio of the 1-hydroxycyclopentanecarbonitrile to the triphosgene is controlled at 1:(0.35-0.55).

As a further improvement of the present disclosure, the present disclosure may further include: subjecting the solution of 1-chlorocyclopentanecarbonitrile in a solvent A prepared to purification: cooling the solution of 1-chlorocyclopentanecarbonitrile in a solvent A prepared to 25° C. to 30° C., adding a sodium bicarbonate solution, stirring and standing to make a resulting mixture settle into layers, and removing an aqueous layer; and repeating the above-mentioned washing process 1 to 3 times to obtain purified 1-chlorocyclopentanecarbonitrile.

As a further improvement of the present disclosure, a molar ratio of the p-nitrochlorobenzene to the zinc powder may be 1:(1-1.8) and preferably 1:1.5.

The amount of zinc powder has a great impact on a product yield. When the zinc powder is added at a small amount, a yield is low. When the molar ratio of the p-nitrochlorobenzene to the zinc powder reaches a specified value, further increasing the amount of zinc powder will basically not change a yield. In the present disclosure, the molar ratio of the p-nitrochlorobenzene to the zinc powder is controlled at 1:(1-1.8), which minimizes the consumption of zinc powder, reduces costs, and saves resources on the premise of ensuring a high yield.

As a further improvement of the present disclosure, the present disclosure may further include: subjecting the compound 1-(4-nitrophenyl)cyclopentanecarbonitrile prepared to purification:

step A: transferring the prepared solution with the compound 1-(4-nitrophenyl)cyclopentanecarbonitrile to a reaction vessel A with a 2% to 5% hydrochloric acid aqueous solution, stirring for 5 min to 20 min, standing to make a resulting mixture settle into layers, and removing an aqueous layer; washing an organic layer 1 to 3 times with water; and recovering the solvent B by atmospheric distillation, and recovering the solvent A by vacuum concentration until no droplets flow out to obtain a 1-(4-nitrophenyl)cyclopentanecarbonitrile concentrate; and step B: adding the 1-(4-nitrophenyl)cyclopentanecarbonitrile concentrate obtained in step A and an 80% to 85% ethanol aqueous solution with a mass 5 to 10 times that of the 1-(4-nitrophenyl)cyclopentanecarbonitrile concentrate to a reaction vessel B, and heating to achieve reflux; after the compound is completely dissolved, continuing the reflux for 20 min to 30 min; cooling a resulting reaction solution for crystallization, and subjecting a resulting mixture to SLS; and water-washing and drying a resulting solid to obtain a 1-(4-nitrophenyl)cyclopentanecarbonitrile refined product.

As a further improvement of the present disclosure, step 2 may specifically include: adding the 1-(4-nitrophenyl)cyclopentanecarbonitrile, 95% to 99% ethanol, water, and the catalyst to a reaction vessel, stirring a resulting mixture, and conducting nitrogen replacement three times and hydrogen replacement three times; heating the resulting mixture to allow a reaction at a temperature of 55° C. to 60° C. and a pressure of 0.4 mpa to 0.6 mpa; after a hydrogen pressure no longer decreases, keeping a resulting reaction solution at the temperature for 0.5 h to 1.0 h, and subjecting the resulting reaction solution to SLS; cooling a resulting liquid to 10° C. to 15° C. and keeping at the temperature for 0.5 h to 1.0 h for crystallization; and subjecting a resulting mixture to SLS, and water-washing and oven-drying a resulting solid to obtain the 1-(4-aminophenyl)cyclopentanecarbonitrile; where the catalyst may be one from the group consisting of Pt/C and Pd/C.

Nitroreduction is mostly achieved through Pd/C or Pt/C-catalyzed hydrogen reduction or Zn, Fe, or Sn-catalyzed reduction. In the Zn, Fe, or Sn-catalyzed reduction, iron, zinc, or stannum sludge will be produced, which pollutes the environment, is difficult to treat subsequently, and reduces a yield. The Pd/C or Pt/C catalyst used in the present disclosure has high catalytic efficiency and can be recycled, which is cost-effective and environmentally-friendly.

Compared with the prior art, the present disclosure has the following beneficial effects.

(1) In the present disclosure, p-nitrochlorobenzene is used as a raw material to prepare 1-(4-aminophenyl)cyclopentanecarbonitrile, which has the advantages of easily-available raw materials, mild reaction conditions, convenient operations, and high yield.

(2) In the present disclosure, the Grignard reagent substitution reaction is used to prepare 1-(4-nitrophenyl)cyclopentanecarbonitrile, which avoids a dangerous nitration process and reduces the safety risk of the process. Moreover, the reaction avoids the generation of o-nitro by-products that will be produced in a nitration process due to low reaction selectivity, which improves a reaction yield.

(3) In the present disclosure, the Pd/C or Pt/C-catalyzed hydrogenation is used to reduce nitro, which avoids the generation of a large amount of iron sludge that will be produced in reduction with iron powder, and thus is environmentally-friendly.

(4) In the present disclosure, BTC is used as a chlorination reagent, which avoids the use of highly-corrosive $POCl_3$ and phosphoric acid, reduces environmental pollution, avoids high-temperature reaction conditions, lowers equipment requirements, and is suitable for industrial large-scale production.

DETAILED DESCRIPTION OF THE EMBODIMENTS

The present disclosure will be described in detail below in conjunction with specific examples, such that those skilled in the art can understand the present disclosure more comprehensively. The specific examples are merely used to illustrate the technical solutions of the present disclosure and do not limit the present disclosure in any way.

Term Explanation:

| Abbreviation | Full name |
|---|---|
| BTC | Bis(trichloromethyl)carbonate; triphosgene |
| THF | Tetrahydrofuran |

Example 1

Preparation of 1-(4-nitrophenyl)cyclopentanecarbonitrile:

Step 1: 245.0 g of xylene and 25.9 g of triphosgene were thoroughly mixed for later use.

Step 2: 27.8 g of 1-hydroxycyclopentanecarbonitrile and 170.0 g of xylene were added into a reaction vessel, and a resulting mixture was stirred and heated to 60° C.; a solution of triphosgene in xylene was added dropwise at a temperature controlled to 60° C. to 65° C.; and after the dropwise addition was completed, a resulting mixture was heated to allow a reaction at reflux for 2 h to obtain a 1-chlorocyclopentanecarbonitrile solution.

Step 3: 100 g of THF and 39.4 g of p-nitrochlorobenzene were thoroughly mixed for later use.

Step 4: 300.0 g of diethyl ether and 16.4 g of a zinc powder were added into a reaction vessel, nitrogen replacement was conducted three times, and a resulting mixture was stirred and heated to 50° C. under nitrogen protection; 12.0 g of a p-nitrochlorobenzene solution was added dropwise, and a resulting mixture was stirred for 20 min; after success initiation, a p-nitrochlorobenzene solution was further added dropwise at a temperature controlled to 50° C. to 55° C.; after the dropwise addition was completed, a resulting mixture was heated to allow a reaction at reflux for 2 h; and a reaction solution was cooled to 25° C. and then subjected to SLS to obtain a p-nitrochlorobenzene-zinc reagent.

Step 5: The 1-chlorocyclopentanecarbonitrile solution prepared in step 2 and 2.0 g of $Li_2CuCl_4$ were added into a reaction vessel, and a resulting mixture was stirred and cooled to 10° C.; the p-nitrochlorobenzene-zinc reagent prepared in step 4 was added dropwise; after the dropwise addition was completed, a resulting mixture was kept at 15° C. for 2 h to complete a reaction; a resulting reaction solution was transferred to a flask with 200 ml of a 3% hydrochloric acid aqueous solution, and a resulting mixture was stirred for 10 min and stood to settle into layers; an aqueous layer was removed, and an organic layer was washed with water twice; and diethyl ether was recovered by atmospheric distillation, and xylene was recovered by vacuum concentration until no droplets flowed out to obtain a 1-(4-nitrophenyl)cyclopentanecarbonitrile concentrate.

Step 6: The 1-(4-nitrophenyl)cyclopentanecarbonitrile concentrate prepared in step 5 and 500 g of an 85% ethanol aqueous solution were added into a four-necked flask, and a resulting mixture was heated to achieve reflux; after the compound was completely dissolved, the reflux was continued for 20 min; a resulting reaction solution was cooled for crystallization and then filtered; and a filter cake was rinsed with water, drained, and dried to obtain a 1-(4-nitrophenyl)cyclopentanecarbonitrile refined product, with a yield of 75.9% (relative to the raw material 1-hydroxycyclopentanecarbonitrile).

Example 2

Preparation of 1-(4-nitrophenyl)cyclopentanecarbonitrile:

Step 1: 245 g of toluene and 40.8 g of triphosgene were thoroughly mixed for later use.

Step 2: 27.8 g of 1-hydroxycyclopentanecarbonitrile and 170.0 g of toluene were added into a reaction vessel, and a resulting mixture was stirred and heated to 55° C.; a solution of triphosgene in toluene was added dropwise at a temperature controlled to 60° C. to 65° C.; and after the dropwise addition was completed, a resulting mixture was heated to allow a reaction at reflux for 2 h to obtain a solution of 1-chlorocyclopentanecarbonitrile in toluene.

Step 3: 100 g of THF and 39.4 g of p-nitrochlorobenzene were thoroughly mixed for later use.

Step 4: 300.0 g of THF and 29.5 g of a zinc powder were added into a reaction vessel, nitrogen replacement was conducted three times, and a resulting mixture was stirred and heated to 45° C. under nitrogen protection; 12.0 g of a p-nitrochlorobenzene solution was added dropwise, and a resulting mixture was stirred for 20 min; after success initiation, a p-nitrochlorobenzene solution was further added dropwise at a temperature controlled to 50° C. to 55° C.; after the dropwise addition was completed, a resulting mixture was heated to allow a reaction at reflux for 2 h; and a reaction solution was cooled to 25° C. and then subjected to SLS to obtain a p-nitrochlorobenzene-zinc reagent.

Step 5: The solution of 1-chlorocyclopentanecarbonitrile in toluene prepared in step 2 and 2.0 g of $Li_2CuCl_4$ were added into a reaction vessel, and a resulting mixture was stirred and cooled to 5° C.; the p-nitrochlorobenzene-zinc reagent prepared in step 4 was added dropwise; after the dropwise addition was completed, a resulting mixture was kept at 15° C. for 2 h to complete a reaction; a resulting reaction solution was transferred to a flask with 200 ml of a 3% hydrochloric acid aqueous solution, and a resulting mixture was stirred for 20 min and stood to settle into layers; an aqueous layer was removed, and an organic layer was washed with water twice; and THF was recovered by atmospheric distillation, and toluene was recovered by vacuum concentration until no droplets flowed out to obtain a 1-(4-nitrophenyl)cyclopentanecarbonitrile concentrate.

Step 6: The 1-(4-nitrophenyl)cyclopentanecarbonitrile concentrate prepared in step 5 and 500 g of an 80% ethanol aqueous solution were added into a four-necked flask, and a resulting mixture was heated to achieve reflux; after the compound was completely dissolved, the reflux was continued for 30 min; a resulting reaction solution was cooled for crystallization and then filtered; and a filter cake was rinsed with water, drained, and dried to obtain a 1-(4-nitrophenyl)

cyclopentanecarbonitrile refined product, with a yield of 73.4% (relative to the raw material 1-hydroxycyclopentanecarbonitrile).

Example 3

1) Preparation of 1-(4-nitrophenyl)cyclopentanecarbonitrile:

Step 1: 245.0 g of toluene and 37.1 g of triphosgene were thoroughly mixed to obtain a solution of triphosgene in toluene for later use.

Step 2: 27.8 g of 1-hydroxycyclopentanecarbonitrile and 170.0 g of toluene were added into a reaction vessel, and a resulting mixture was stirred and heated to 55° C.; the solution of triphosgene in toluene prepared in step 1 was added dropwise at a temperature controlled to 60° C. to 65° C.; and after the dropwise addition was completed, a resulting mixture was heated to allow a reaction at reflux for 2 h to obtain a 1-chlorocyclopentanecarbonitrile solution, with a reaction yield of 94%.

Step 3: 100 g of THF and 39.4 g of p-nitrochlorobenzene were thoroughly mixed for later use.

Step 4: 300.0 g of THF and 24.6 g of a zinc powder were added into a reaction vessel, nitrogen replacement was conducted three times, and a resulting mixture was stirred and heated to 45° C. to 50° C. under nitrogen protection; 12.0 g of a p-nitrochlorobenzene solution was added dropwise, and a resulting mixture was stirred for 15 min; after success initiation, a p-nitrochlorobenzene solution was further added dropwise at a temperature controlled to 50° C. to 55° C.; after the dropwise addition was completed, a resulting mixture was heated to allow a reaction at reflux for 1 h to 2 h; and a reaction solution was cooled to 20° C. and then subjected to SLS to obtain a p-nitrochlorobenzene-zinc reagent.

Step 5: The solution of 1-chlorocyclopentanecarbonitrile in toluene prepared in step 2 and 2.0 g of Li$_2$CuCl$_4$ were added into a reaction vessel, and a resulting mixture was stirred and cooled to 5° C.; the p-nitrochlorobenzene-zinc reagent prepared in step 4 was added dropwise; after the dropwise addition was completed, a resulting mixture was kept at 20° C. for 1 h to complete a reaction; a resulting reaction solution was transferred to a flask with 200 ml of a 2% hydrochloric acid aqueous solution, and a resulting mixture was stirred for 10 min and stood to settle into layers; an aqueous layer was removed, and an organic layer was washed with water twice; and THF was recovered by atmospheric distillation, and toluene was recovered by vacuum concentration until no droplets flowed out to obtain a 1-(4-nitrophenyl)cyclopentanecarbonitrile concentrate.

Step 6: The 1-(4-nitrophenyl)cyclopentanecarbonitrile concentrate prepared in step 5 and 500 g of an 80% ethanol aqueous solution were added into a four-necked flask, and a resulting mixture was heated to achieve reflux; after the compound was completely dissolved, the reflux was continued for 20 min; a resulting reaction solution was cooled for crystallization and then filtered; and a filter cake was rinsed with water, drained, and dried to obtain a 1-(4-nitrophenyl) cyclopentanecarbonitrile refined product, with a yield of 87.5% (relative to the raw material 1-hydroxycyclopentanecarbonitrile).

2) Preparation of 1-(4-aminophenyl)cyclopentanecarbonitrile:

45.0 g of the 1-(4-nitrophenyl)cyclopentanecarbonitrile refined product, 300.0 g of 95% ethanol, 50.0 g of drinking water, and 2.0 g of Pd/C were added into a reaction vessel, nitrogen replacement was conducted three times, and hydrogen replacement was conducted three times; a resulting mixture was stirred and heated to allow a reaction at a temperature of 55° C. to 60° C. and a pressure of 0.4 mpa to 0.6 mpa; after a hydrogen pressure no longer decreased, a resulting reaction solution was kept at the temperature for 0.5 h to complete the reaction, and then filtered while hot to remove Pd/C (which was recovered for later use); a resulting filtrate was cooled to 10° C. and kept at the temperature for 1 h for crystallization; and a resulting mixture was filtered, and a filter cake was washed with water and then oven-dried to obtain a 1-(4-aminophenyl)cyclopentanecarbonitrile finished product, with a yield of 86.1%.

Example 4

1) Preparation of 1-(4-nitrophenyl)cyclopentanecarbonitrile:

Step 1: 270.0 g of toluene and 55.7 g of triphosgene were thoroughly mixed for later use.

Step 2: 41.7 g of 1-hydroxycyclopentanecarbonitrile and 1020.0 g of toluene were added into a reaction vessel, and a resulting mixture was stirred and heated to 60° C.; a solution of triphosgene in toluene was added dropwise at a temperature controlled to 60° C. to 65° C.; and after the dropwise addition was completed, a resulting mixture was heated to allow a reaction at reflux for 1 h to obtain a 1-chlorocyclopentanecarbonitrile solution.

Step 3: 150 g of THF and 59.1 g of p-nitrochlorobenzene were thoroughly mixed for later use.

Step 4: 300.0 g of THF and 37.0 g of a zinc powder were added into a reaction vessel, nitrogen replacement was conducted three times, and a resulting mixture was stirred and heated to 50° C. under nitrogen protection; 10.0 g of a p-nitrochlorobenzene solution was added dropwise, and a resulting mixture was stirred for 30 min; after success initiation, a p-nitrochlorobenzene solution was further added dropwise at a temperature controlled to 50° C. to 55° C.; after the dropwise addition was completed, a resulting mixture was heated to allow a reaction at reflux for 1 h; and a reaction solution was cooled to 30° C. and then subjected to SLS to obtain a p-nitrochlorobenzene-zinc reagent.

Step 5: The 1-chlorocyclopentanecarbonitrile solution prepared in step 2 and 3.0 g of Li$_2$CuCl$_4$ were added into a reaction vessel, and a resulting mixture was stirred and cooled to 10° C.; the p-nitrochlorobenzene-zinc reagent prepared in step 4 was added dropwise; after the dropwise addition was completed, a resulting mixture was kept at 15° C. for 2 h to complete a reaction; a resulting reaction solution was transferred to a flask with 300 ml of a 5% hydrochloric acid aqueous solution, and a resulting mixture was stirred for 5 min and stood to settle into layers; an aqueous layer was removed, and an organic layer was washed with water twice; and THF was recovered by atmospheric distillation, and toluene was recovered by vacuum concentration until no droplets flowed out to obtain a 1-(4-nitrophenyl)cyclopentanecarbonitrile concentrate.

Step 6: The 1-(4-nitrophenyl)cyclopentanecarbonitrile concentrate prepared in step 5 and 750 g of an 85% ethanol aqueous solution were added into a four-necked flask, and a resulting mixture was heated to achieve reflux; after the compound was completely dissolved, the reflux was continued for 30 min; a resulting reaction solution was cooled for crystallization and then filtered; and a filter cake was rinsed with water, drained, and dried to obtain a 1-(4-nitrophenyl) cyclopentanecarbonitrile refined product, with a yield of 88.2% (relative to the raw material 1-hydroxycyclopentanecarbonitrile).

2) Preparation of 1-(4-aminophenyl)cyclopentanecarbonitrile:

70.0 g of the 1-(4-nitrophenyl)cyclopentanecarbonitrile refined product, 465.0 g of 95% ethanol, 80.0 g of drinking water, and 3.5 g of Pt/C were added into a reaction vessel, nitrogen replacement was conducted three times, and hydrogen replacement was conducted three times; a resulting mixture was stirred and heated to allow a reaction at a temperature of 55° C. to 60° C. and a pressure of 0.4 mpa to 0.6 mpa; after a hydrogen pressure no longer decreased, a resulting reaction solution was kept at the temperature for 0.5 h to complete the reaction, and then filtered while hot to remove Pt/C (which was recovered for later use); a resulting filtrate was cooled to 15° C. and kept at the temperature for 1 h for crystallization; and a resulting mixture was filtered, and a filter cake was washed with water and then oven-dried to obtain a 1-(4-aminophenyl)cyclopentanecarbonitrile finished product, with a yield of 85.5%.

The implementations of the present disclosure are described in detail above, but the present disclosure is not limited to the above implementations. Several modifications and improvements can be made by those of ordinary skill in the art without departing from the present disclosure, and such modifications and improvements should also be deemed as falling within the protection scope of the present disclosure.

What is claimed is:

1. A preparation method of 1-(4-aminophenyl)cyclopentanecarbonitrile, comprising the following steps:
    step 1: in the presence of $Li_2CuCl_4$, adding a solution of p-nitrochlorobenzene-zinc in a second solvent dropwise to a solution of 1-chlorocyclopentanecarbonitrile in a first solvent to prepare a compound 1-(4-nitrophenyl)cyclopentanecarbonitrile; and
    step 2: subjecting the compound 1-(4-nitrophenyl)cyclopentanecarbonitrile obtained in step 1 to a nitroreduction reaction in a third solvent under the action of a catalyst to prepare the compound 1-(4-aminophenyl)cyclopentanecarbonitrile;
    wherein a reaction equation is as follows:

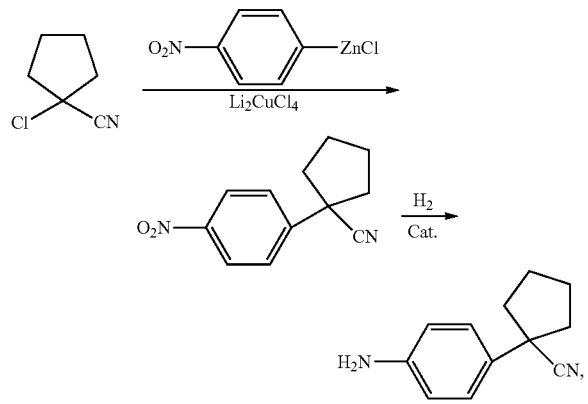

the first solvent used in step 1 is one from the group consisting of toluene, xylene, benzene, diethyl ether, chloroform, and tetrahydrofuran (THF);
the second solvent used in step 1 is one from the group consisting of toluene, diethyl ether, THF, and dimethyl sulfoxide (DMSO); and
the third solvent used in step 2 is one from the group consisting of ethanol, methanol, and isobutanol.

2. The preparation method of according to claim 1, wherein in step 1, the solution of 1-chlorocyclopentanecarbonitrile in the first solvent is prepared as follows:
    adding 1-hydroxycyclopentanecarbonitrile and the first solvent into a reaction vessel, stirring, and heating to 55° C. to 60° C.; adding a solution of 10% to 17% triphosgene in the first solvent dropwise at a temperature controlled to 60° C. to 65° C.; and after the dropwise addition is completed, heating a resulting mixture to allow a reaction at reflux for 1 h to 2 h to obtain the solution of 1-chlorocyclopentanecarbonitrile in the first solvent, wherein a reaction equation is as follows:

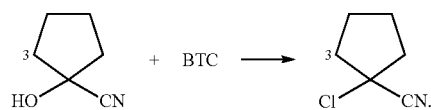

3. The preparation method of according to claim 1, wherein in step 1, the solution of p-nitrochlorobenzene-zinc in the second solvent is prepared as follows:
    adding the second solvent and a zinc powder into a reaction vessel, stirring, and heating to 45° C. to 50° C. under nitrogen protection; adding a solution of 5% to 10% p-nitrochlorobenzene in the second solvent dropwise, and stirring for 15 min to 30 min; after success initiation, further adding the solution of p-nitrochlorobenzene in the second solvent dropwise at a temperature controlled to 50° C. to 55° C.; after the dropwise addition is completed, heating to achieve reflux for 1 h to 2 h; and cooling to 20° C. to 30° C., and conducting a solid-liquid separation (SLS) to obtain the solution of p-nitrochlorobenzene-zinc in the second solvent, wherein a reaction equation is as follows:

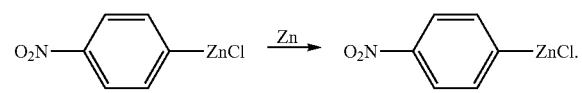

4. The preparation method of according to claim 1, wherein step 1 specifically comprises: adding the solution of 1-chlorocyclopentanecarbonitrile in the first solvent and the $Li_2CuCl_4$ to a reaction vessel, stirring, and cooling to 5° C. to 10° C.; adding the solution of p-nitrochlorobenzene-zinc in the second solvent dropwise at a temperature controlled to 10° C. to 15° C.; and after the dropwise addition is completed, keeping a resulting mixture at 15° C. to 20° C. for 1 h to 2 h to obtain a solution with the compound 1-(4-nitrophenyl)cyclopentanecarbonitrile.

5. The preparation method according to claim 2, wherein a molar ratio of the 1-hydroxycyclopentanecarbonitrile to the triphosgene is 1:(0.35-0.55).

6. The preparation method according to claim 2, further comprising: subjecting the solution of 1-chlorocyclopentanecarbonitrile in the first solvent prepared to purification: cooling the solution of 1-chlorocyclopentanecarbonitrile in the first solvent prepared to 25° C. to 30° C., adding a sodium bicarbonate solution, stirring, washing, and standing to make a resulting mixture settle into layers, and removing an aqueous layer; and repeating the above-mentioned washing process 1 to 3 times to obtain purified 1-chlorocyclopentanecarbonitrile.

7. The preparation method according to claim 3, wherein a molar ratio of the compound p-nitrochlorobenzene to the zinc powder is 1:(1-1.8).

8. The preparation method according to claim 4, further comprising: treating the solution with the compound 1-(4-nitrophenyl)cyclopentanecarbonitrile as follows:
   step A: transferring the prepared solution with the compound 1-(4-nitrophenyl)cyclopentanecarbonitrile to a first reaction vessel with a 2% to 5% hydrochloric acid aqueous solution, stirring for 5 min to 20 min, standing to make a resulting mixture settle into layers, and removing an aqueous layer; washing an organic layer 1 to 3 times with water; and recovering the second solvent by atmospheric distillation, and recovering the first solvent by vacuum concentration until no droplets flow out to obtain a 1-(4-nitrophenyl)cyclopentanecarbonitrile concentrate; and
   step B: adding the 1-(4-nitrophenyl)cyclopentanecarbonitrile concentrate obtained in step A and an 80% to 85% ethanol aqueous solution with a mass 5 to 10 times a mass of the 1-(4-nitrophenyl)cyclopentanecarbonitrile concentrate to a second reaction vessel, and heating to achieve reflux; after the compound is completely dissolved, continuing the reflux for 20 min to 30 min; cooling for crystallization, and conducting an SLS; and water-washing and drying a resulting solid to obtain a 1-(4-nitrophenyl)cyclopentanecarbonitrile refined product.

9. The preparation method according to claim 1, wherein step 2 specifically comprises: adding the 1-(4-nitrophenyl)cyclopentanecarbonitrile, 95% to 99% ethanol, water, and the catalyst to a reaction vessel, stirring, and conducting nitrogen replacement three times and hydrogen replacement three times; heating to allow a reaction at a temperature of 55° C. to 60° C. and a pressure of 0.4 mpa to 0.6 mpa; after a hydrogen pressure no longer decreases, keeping at the temperature for 0.5 h to 1.0 h, and conducting a first SLS; cooling a resulting liquid to 10° C. to 15° C. and keeping at the temperature for 0.5 h to 1.0 h for crystallization; and conducting a second SLS, and water-washing and oven-drying a resulting solid to obtain the 1-(4-aminophenyl)cyclopentanecarbonitrile; wherein the catalyst is one from the group consisting of Pt/C and Pd/C.

* * * * *